Figure 1:
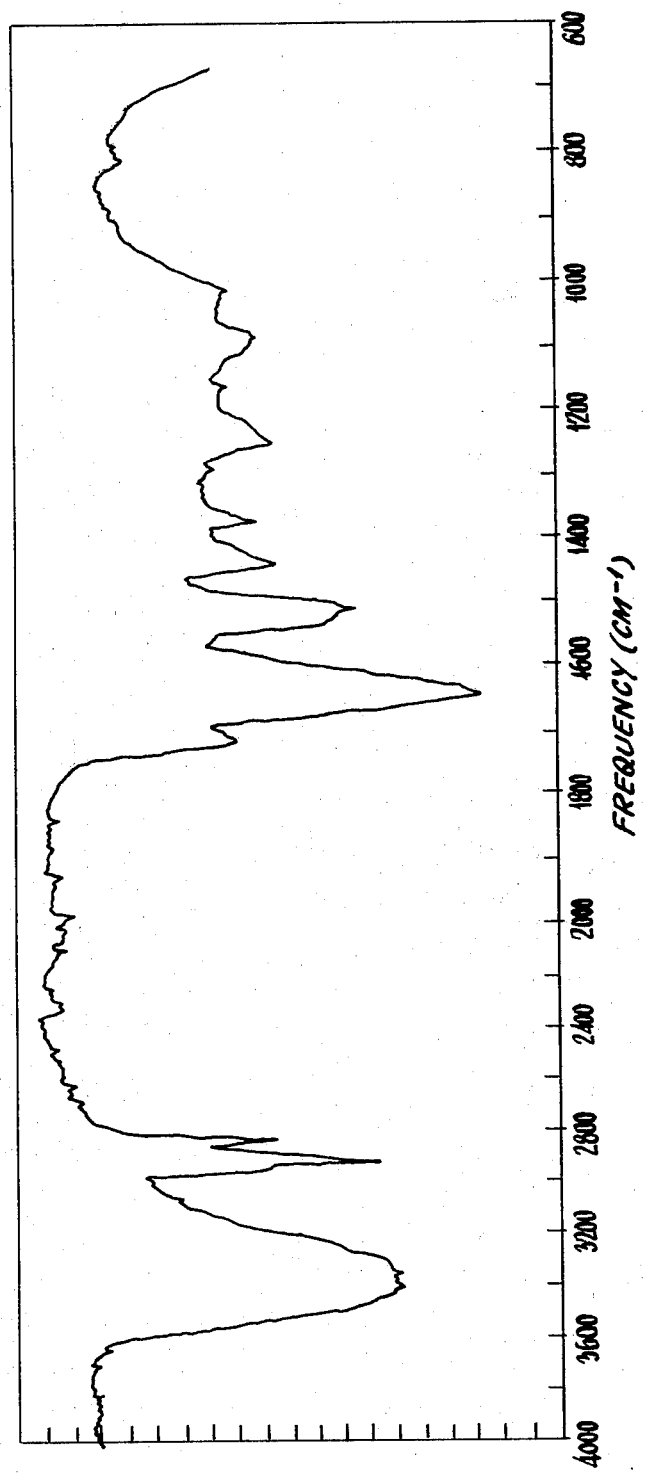

United States Patent [19]

Onishi et al.

[11] 4,254,224

[45] Mar. 3, 1981

[54] FERMENTATION METHOD FOR PRODUCING ANTIBIOTIC A43F

[75] Inventors: Janet C. Onishi, Mountainside; Gerald L. Rowin, Kendall Park; John E. Miller, Jr., Edison, all of N.J.

[73] Assignee: Merck & Co., Inc., Rahway, N.J.

[21] Appl. No.: 56,488

[22] Filed: Jul. 11, 1979

Related U.S. Application Data

[62] Division of Ser. No. 19,679, Mar. 12, 1979, Pat. No. 4,201,771.

[51] Int. Cl.$^3$ ............................................. C12P 21/04
[52] U.S. Cl. ..................................... 435/71; 435/911
[58] Field of Search .......................................... 435/71

[56] References Cited

U.S. PATENT DOCUMENTS

| | | | |
|---|---|---|---|
| 3,824,305 | 7/1974 | Hamill et al. | 435/71 |
| 3,892,732 | 7/1975 | Abe et al. | 435/71 |

*Primary Examiner*—Alvin E. Tanenholtz
*Attorney, Agent, or Firm*—Frank M. Mahon; Julian S. Levitt

[57] ABSTRACT

The antibiotic A43F is active against a variety of plant pathogenic fungi. The antibiotic A43F is produced by growing an as yet unclassified species of fungus (ATCC No. 20529) on suitable fermentation media and isolating the bioactive component therefrom.

2 Claims, 2 Drawing Figures

FERMENTATION METHOD FOR PRODUCING ANTIBIOTIC A43F

This is a division of application Ser. No. 19,679, filed Mar. 12, 1979 and now U.S. Pat. No. 4,201,771.

SUMMARY OF THE INVENTION

This invention relates to a new antifungal antibiotic agent. More particularly, the instant invention relates to a new antifungal antibiotic agent hereinafter referred to as A43F. The invention encompasses the antibiotic in dilute forms, as crude concentrates and in pure forms.

It is an object of the instant invention to provide a new and useful antifungal antibiotic which is highly effective in inhibiting the growth of a wide variety of plant pathogens. Another object is to provide a process for preparing the novel antibiotic substance by the fermentation of a nutrient media with an as yet unclassified species of fungus initially isolated from a fluff sample taken from a chicken incubator. Other objects will be apparent from the detailed description of the instant invention hereinafter provided.

In its composition of matter aspect, therefore, the instant invention may be described as residing in the concept of a novel antibiotic characterized by having the following structural formula:

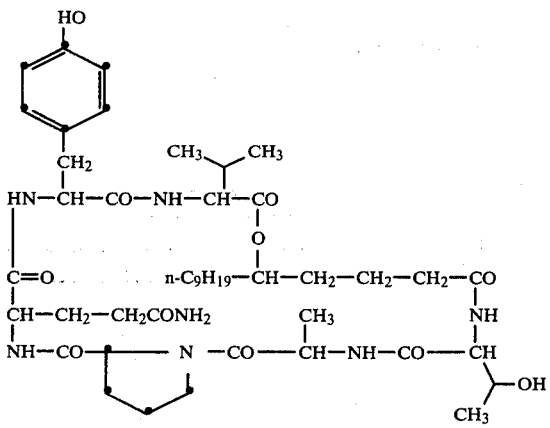

This structure has been assigned to antibiotic A43F on the basis of various observed physical and chemical characteristics hereinafter described. The structure has not been determined with certitude, however, and it is to be understood that the structure presented above represents a working hypothesis merely.

Antibiotic A43F inhibits the growth of a variety of fungi which are pathogenic to plant life including *Puccinia recondita* f. sp. *tritici, Piricularia oryzae, Phytophthora infestans, Alternaria solani* and *Erysiphe polygoni*. It is contemplated, therefore, that antifungally effective amounts of antibiotic A43F will be applied as an agricultural fungicide in the treatment and control of pathogenic fungus infestations of plants. The antifungal activity of antibiotic A43F has been confirmed in vivo employing standard greenhouse bioassay techniques.

As pointed out above, antibiotic A43F is prepared by growing under controlled conditions an as yet unclassified species of fungus initially isolated from a fluff sample taken from a chicken incubator. This fungus species has been designated MF 4683 in the culture collection of MERCK & CO., Inc., Rahway, N.J. A viable culture thereof has been placed on permanent deposit with the culture collection of the American Type Culture Collection, 12301 Parklawn Dr., Rockville, Md. 20852, and has been assigned accession number ATCC No. 20529.

CHEMICAL AND PHYSYCAL CHARACTERISTICS OF ANTIBIOTIC A43F

Antibiotic A43F is a white amorphous solid of elemental composition $C_{45}H_{71}N_7O_{11}$. Molecular weight 885 was determined by high-resolution mass spectrometric measurement at m/e 867 (M—$H_2O$): found 867.5056, calculated 867.5106. The molecular weight 885 was determined by field desorption mass spectrometry.

Ultraviolet absorption of antibiotic A43F was measured in neutral and acid (0.01 N HCl) methanol and in basic (0.01 N NaOH) methanol.

Neutral and Acid Methanol $\lambda$max 225 nm, $E^{1\%}=230$ $\lambda$max 278 nm, $E^{1\%}=38$ $\lambda$max 284 nm, (sh.), $E^{1\%}=33$

Basic Methanol $\lambda$max 245 nm, $E^{1\%}=200$ $\lambda$max 294 nm, $E^{1\%}=50$ The infrared spectrum of antibiotic A43F in KBr is shown in FIG. 1.

Figure 2:
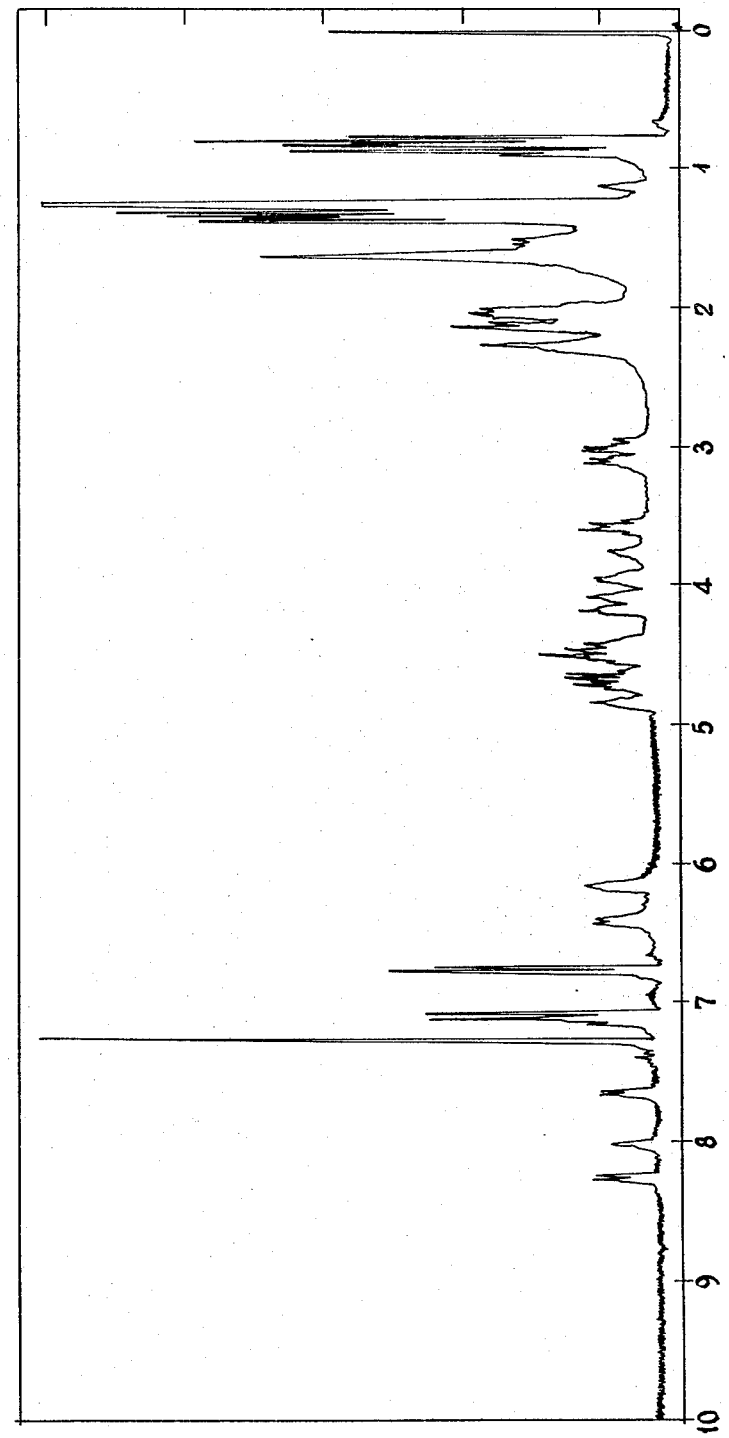

The $^1$H NMR spectrum of antibiotic A43F is shown in FIG. 2. Chemical shifts are given in ppm (parts-per-million) relative to internal tetramethylsilane. The solvent is $CDCl_3$.

$^{13}$C NMR spectra were recorded in $CDCl_3$: $CD_3OD$ (4:1) at a concentration of 60 mg./0.45 ml. Chemical shifts for all 45 carbon atoms are given in the following list in ppm relative to internal tetramethylsilane. Signals representing more than one carbon atom are indicated by the number of carbon atoms in brackets after the chemical shift figure.

14.1, 16.0, 18.3, 19.1, 20.4, 21.2, 22.8, 24.8, 25.6, 27.0, 29.5−, 29.5+, 29.7 [3], 30.1, 3.20, 32.6, 33.0, 34.6, 35.9, 37.9, 47.8, 48.1, 53.9, 55.8, 58.0, 59.8, 61.6, 67.7, 74.8, 115.7 [2], 127.9, 130.4, [2], 156.0, 171.7, 171.9, 172.4 [2], 172.9, 173.0, 174.6, 176.2 ppm.

Antibiotic A43F contains one equivalent each of L-valine, L-glutamine, L-proline, D-alanine, D-tyrosine, D-allothreonine and δ-hydroxymyristic acid.

The structure of antibiotic A43F (as determined by high-resolution mass spectrometry, $^1$H and $^{13}$C NMR and IR spectroscopy, amino acid analysis of the antibiotic and its tyrosine O-methyl ether derivatives is shown below and in formula I above.

$$\begin{array}{c}
\text{HO} \\
| \\
\text{[phenyl ring]} \\
| \\
\text{CH}_2 \qquad \text{CH}_3 \quad \text{CH}_3 \\
\text{HN—CH—CO—NH—CH—CO} \\
| \qquad\qquad\qquad\qquad\quad | \\
\text{C=O} \qquad n\text{-C}_9\text{H}_{19}\text{—CH—CH}_2\text{—CH}_2\text{—CH}_2\text{—CO} \\
| \qquad\qquad\qquad\qquad | \\
\text{CH—CH}_2\text{—CH}_2\text{CONH}_2 \qquad \text{CH}_3 \qquad\qquad \text{NH} \\
| \qquad\qquad\qquad\qquad\qquad\qquad\qquad | \\
\text{NH—CO—[proline]—N—CO—CH—NH—CO—CH} \\
\qquad\qquad\qquad\qquad\qquad\qquad\qquad\qquad\qquad \rangle\text{—OH} \\
\qquad\qquad\qquad\qquad\qquad\qquad\qquad\qquad\qquad \text{CH}_3
\end{array}$$

PRODUCTION OF ANTIBIOTIC A43F—FERMENTATION PROCESS

The standard operating procedure for the production of antibiotic A43F by fermentation of the fungus ATCC No. 20529 is described below:

1. "A" Stage

The culture (ATCC No. 20529) is maintained in frozen vials at −70° to −90° C. To obtain the frozen vegetative stage, the culture is grown in seed media at 28° C., 220 rpm for one day. 20% glycerol is added and the mixture subdivided into 2 ml aliquot per vial. The vials are aseptically sealed and stored in the gaseous phase of liquid nitrogen.

2. "B" Stage

Vessel: 250 ml 3 baffled Erlenmeyer flask with 50 ml. per flask.
Medium:

| | WT/VOL |
|---|---|
| Corn steep liquor | 0.5% |
| Tomato paste | 4.0% |
| Oat flour No. 36 | 1.0% |
| Glucose | 1.0% |
| *Trace element mix No. 2 | 1.0% vol/vol |

*Trace element mix No. 2 (Final "B" Stage Medium Concentration)

| | mgm/l |
|---|---|
| $FeSO_4 \cdot 7H_2O$ | 10.0 |
| $MnSO_4 \cdot 4H_2O$ | 10.0 |
| $CuCl_2 \cdot 2H_2O$ | 0.25 |
| $CaCl_2$ | 1.0 |
| $H_3BO_3$ | 0.56 |
| $(NH_4)_6Mo_7O_{24} \cdot 4H_2O$ | 0.19 |
| $ZnSO_4 \cdot 7H_2O$ | 2.0 |
| Pre-sterile pH | 6.8 |

Inoculum: 2 ml from frozen vial.
Incubation: 24 hours at 150 rpm and 28° C.
Sterility: Streak plates and gram stain.

3. "C" Stage

Vessel: 2 liter 3 baffled Erlenmeyer flask with 500 ml.
Media: Same as "B" Stage.
Inoculum: 10 ml. from "B" Stage.
Incubation: 24 hours at 150 rpm and 28° C.
Sterility: Streak plates and gram stain.

4. "D" Stage

Vessel: 50 gallon stainless steel fermentor.
Medium:

| | WT/VOL |
|---|---|
| Corn steep liquor | 0.5% |
| Tomato paste | 4.0% |
| Oat flour | 1.0% |
| Dextrose | 1.0% |
| $FeSO_4 \cdot 7H_2O$ | 0.001% |
| $MnSO_4 \cdot 4H_2O$ | 0.001% |
| $CuCl_2 \cdot 2H_2O$ | 0.000025% |
| $CaCl_2 \cdot 2H_2O$ | 0.0001% |
| $H_3BO_3$ | 0.000056% |
| $(NH_4)_6Mo_7O_{24} \cdot 4H_2O$ | 0.000019% |
| $ZnSO_4 \cdot 7H_2O$ | 0.2% |
| Polyglycol 2000 | 50 ml |
| Pre-sterile pH | 6.8 |

Sterilization: 15 minutes at 121° C.
Inoculum: 1 liter "C" stage.
Fermentor Volume A.I.: 161 liters.
Cycle Temperature: 28° C.
Airflow: 3 CFM.
Agitation: 150 rpm.
pH control: None.
Cycle time: 24 hours.
Defoamer: None.
Cycle Parameters: pH/12 hours.

| Batch Age (hrs.) | pH |
|---|---|
| AI | 6.8 |
| 0 | 6.6 |
| 12 | 6.2 |

5. "E" Stage

Vessel: 200 gallon stainless steel fermentor.
Medium:

| | WT/VOL |
|---|---|
| Sucrose | 6% |
| Bacto peptone | 1% |
| Ardamine pH | 0.2% |
| Pre-sterile pH | 6.0 |

Sterilization: 15 minutes at 121° C.
Inoculum: 43 liters "D" stage.
Fermentor Volume A.I.: 510 liters.
Cycle Temperature: 24° C.
Airflow: 10 CFM.
Agitation: 130 rpm.
pH Control: None.
Cycle time: 96 hours.
Defoamer: None.
Cycle parameters: pH/12 hours.
Final Activity: 23 mm diameter zone (¼ inch disc whole broth) by *Cochliobolus miyabeanus* (ATCC No. 11608).

| Batch Age (hrs.) | pH |
|---|---|
| 0 | 6.3 |
| 12 | 6.0 |
| 24 | 4.9 |
| 36 | 5.0 |
| 48 | 4.9 |
| 60 | 4.8 |
| 72 | 4.7 |
| 84 | 4.7 |
| 96 | 4.6 |

Seed Media for "A" Stage

| | |
|---|---|
| Corn Steep Liquor | 5 grams |
| Tomato Paste | 40 grams |
| Cerelose | 10 grams |
| *Trace Element Mix No. 2 | 10 ml |
| Distilled $H_2O$ pH 6.8 | 1000 ml |

*Trace Element Mix No. 2 contains the following ingredients:

| | |
|---|---|
| $FeSO_4 \cdot 7H_2O$ | 1000.0 mg/L |
| $MnSO_4 \cdot 4H_2O$ | 1000.0 mg/L |
| $CuCl_2 \cdot 2H_2O$ | 25.0 mg/L |
| $CaCl_2 \cdot 2H_2O$ | 100.0 mg/L |
| $H_3BO_3$ | 56.0 mg/L |
| $(NH_4)_6Mo_7O_{24} \cdot 4H_2O$ | 19.0 mg/L |
| $ZnSO_4 \cdot 7H_2O$ | 200.0 mg/L |
| Distilled $H_2O$ | 1000.ml |

Applicants also have found that antibiotic A43F readily may be produced by static fermentation of the fungus ATCC No. 20529 and that this static fermentation process is preferred where it is desired to achieve increased titer of antibiotic A43F in the fermentation broth. The static fermentation may be carried out by aseptically transferring the contents of a nitrogen frozen vial (2 ml) of the fungus ATCC No. 20529 to a 250 ml.

unbaffled flask containing 40 ml. of seed medium (Seed Media for "A" Stage described above). The flask then is incubated with agitation for 24 hours at 28° C. at 220 R.P.M. After incubation 1 ml of inoculum is aseptically transferred to a 250 ml. unbaffled flask containing 40 ml of production medium and allowed to incubate statically for 4 days at 25° C. The constituents for the production medium are:

| Sucrose | 60 grams |
|---|---|
| Bacto-peptone | 10 grams |
| yeast autolysate (ardamine pH) | 2 grams |
| distilled H₂O | 1000 ml |
| pH 6.0 | |

Upon harvest and assay, the level of antibiotic A43F present has been determined to be approximately 30 μg/ml. By comparison, shake flasks contain less than approximately 1 μg/ml.

ISOLATION OF ANTIBIOTIC A43F

Antibiotic A43F conveniently is isolated from the fermentation broth described above by techniques illustrated in the following flow sheet:

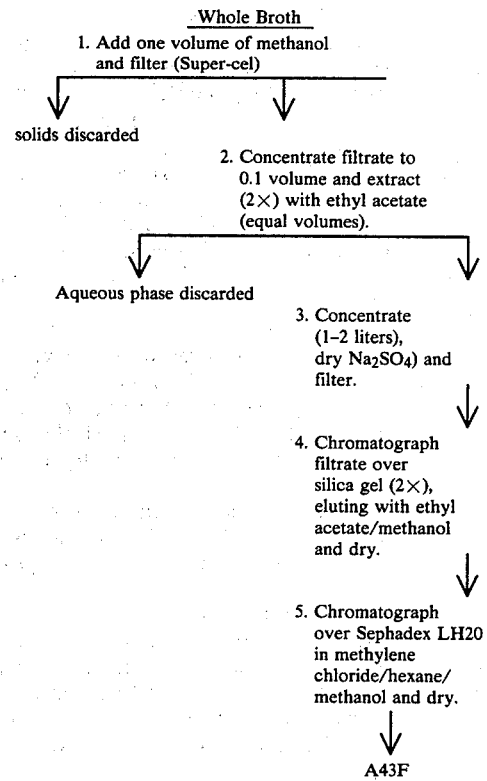

The isolation illustrated above has been carried out as described below.

Step 1

One volume of methanol was added to 50 gallons of the whole broth obtained from the pilot plant fermentation batch described above ("E" Stage) and the mixture was stirred for one hour at room temperature. This step serves two functions: (1) it renders the whole broth filterable and (2) it extracts the antifungal activity from the cells to the filtrate. Super-cell was added to the mixture with stirring and the resultant slurry was filtered through a Super-cel pad.

Step 2

The filtrate was concentrated to one-tenth the volume of the whole broth and extracted two times with an equal volume of ethyl acetate. The combined ethyl acetate layers were concentrated to 1-2 l., dried with sodium sulfate and filtered. Dry weight measurement showed 128 gm. solids at this stage.

Step 3

The ethyl acetate concentrate was chromatographed on 4.5 l. of silica gel formed in ethyl acetate. Elution with ethyl acetate and increasing volumes of methanol in ethyl acetate was made while collecting fractions of 2-3 l. Bioactivity in the effluent was monitored by agar diffusion assays against [Cochliobolus miyabeanus (ATCC No. 11608). Bioactivity appeared as a rather sharp fraction eluting with 30% methanol in ethyl acetate and containing 5.1 gm. of solids.

Step 4

The active fraction (4.6 gm.) from above was rechromatographed on 1.4 l. of silica gel formed in methanol and subsequently washed with acetone and ethyl acetate. The sample was loaded in ethyl acetate and the column eluted with ethyl acetate containing increasing amounts of methanol. Fractions of one liter were collected and assayed for bioactivity as above. Two bioactive fractions eluted with 20% methanol in ethyl acetate were obtained containing 676 mg. and 476 mg. solids, respectively.

Step 5

Both active fractions were purified to homogeneity using Sephadex LH-20 column chromatography as described below. Sephadex LH-20 is a hydroxypropylated dextran gum and is supplied in the form of a dry, free-running powder by Pharmacia Fine Chemicals, Inc., Piscataway, N.J.

A 290 mg. sample obtained from the silica gel chromatography described above was dissolved in methylene chloride:hexane:methanol (10:10:1, 2 ml.) and chromatographed on an Sephadex LH-20 column (150 ml.) equilibrated in the same solvent system. The fractions (8 ml.) were assayed for bioactivity as before and also examined by silica gel thin layer chromatography using the upper phase of the solvent system, butanol:acetic acid:water (5:1:3), as developer. Fractions 33–40 contained the bioactivity as well as a single spot ($R_f$ 0.44) on TLC examination (iodine vapors, UV light, water spray). These fractions were pooled, evaporated to dryness and freeze-dried from dioxane to give 108 mg. of pure antibiotic A43F.

Antibiotic A43F is isolated from the static culture described above by techniques similar to those already described above. For Example, 8,400 ml of a static culture was decanted to remove the liquid portion and the mycelia (about 1080 gm., wet weight) were ground in a Waring blender with 1200 ml. of methanol for about 2 minutes. After addition of one volume of methanol to the homogenate, it was stirred for 4 hours and allowed to stand at room temperature overnight. After filtration, the methanol was removed by distillation in vacuo. The resulting aqueous mileau was brought to 500 ml. with water and extracted two times with 1000 ml. of ethyl acetate. The combined ethyl acetate extracts then are treated as described in Steps 3-5, above, in order to obtain pure antibiotic A43F.

ANTIFUNGAL ACTIVITY OF ANTIBIOTIC A43F

In order to evaluate the antifungal activity of antibiotic A43F, the antibiotic was tested in vivo against a variety of plant pathogenic fungi employing standard green house bioassay techniques. The antibiotic was tested at three levels, 1000 PPM, 500 PPM, and 100 PPM (PPM=parts per million) against various fungal infections in the greenhouse including wheat leaf rust, rice blast, late blight of tomato, early blight of tomato and powdery mildew of been as a protectant (treat and infect same leaf surface) and, similarly as a systemic (treat and infect different leaf surfaces or examine the ability to protect newly-emerging leaves). These tests were carried out as follows:

Leaf Rust of Wheat

Pathogen: *Puccinia recondita* f. sp. *tritici*
Host: Wheat, variety Yorkstar
Growth Conditions: Wheat plants grown to the one leaf stage in the greenhouse on Swiss Farm potting soil in 7 ounce styrafoam pots. Thinned to 3 seedlings per pot. Day temperatures 20°-28° C.; night temperatures 15°-20° C. Soluble 20-20-20 fertilizer applied weekly.
Treatment: Test solutions or suspensions of candidate compounds sprayed on both leaf surfaces to run-off with a No. 152 DeVilbiss atomizer at 10 psi. Formulations are prepared by dissolving compounds in methanol-Tween 20 mixture and bringing to volume with deionized water.
Inoculation: Two days after treatment a uredospore suspension (20,000/ml.) is sprayed on both leaf surfaces with a No. 152 DeVilbiss atomizer at 10 psi. The inoculum is sprayed to a point just before run-off (non-coalescing droplets). The inoculated plants are maintained at 100 percent relative humidity and 21° C. for 24 hours.
Incubation: The treated and inoculated plants are incubated in the greenhouse ((15°-20° C. night temperatures; 20°-28° C. day temperatures) until symptoms appear.
Standard of Comparison: Maneb: [[1,2-Ethanediylbis[carbamodithioato]]-(2-)]manganese.

Disease index: $\dfrac{\text{number of lesions per basal leaf}}{\text{leaf area}}$ Literature Citation: Davis, D., L. Chaiet, J. W. Rothrock, J. Deak, S. Halmos, and J. D. Garber, 1960. Chemotherapy of Cereal Rusts with a New Antibiotic. Phytopathology 50: 841-843.

Rice Blast

Pathogen: *Piricularia oryzae*
Host: Rice, variety Calusa No. 2.
Growth Conditions: Rice plants grown to 5 leaf stage in greenhouse on Swiss Farm Potting soil in 7 ounce styrafoam pots. Thinned to 3 seedlings per pot. Day temperature 20°-28° C.; night temperature 15°-20° C. Soluble 20-20-20 fertilizer applied weekly.
Treatment: Test solutions or suspensions of candidate compounds sprayed on both leaf surfaces to run-off with a No. 152 DeVilbiss atomizer at 10 psi. Formulations are prepared by dissolving compounds in methanol-Tween 20 mixture and bringing to volume with deionized water.
Inoculation: Two days after treatment a spore suspension (50,000/ml) is sprayed on the upper leaf surface with a No. 152 DeVilbiss atomizer at 10 psi. The inoculum is sprayed to a point just before run-off (non coalescing droplets). The inoculated plants are maintained at 100 percent relative humidity and 28° C. for 24 hours.
Incubation: The treated and inoculated plants are incubated in the greenhouse (15°-20° C. night temperatures; 20°-28° C. day temperatures) until symptoms appear.
Standard of Comparison: Hinosan: O-Ethyl 5,5-diphenylphosphorodithioate.

Disease index: $\dfrac{\text{number of lesions per 4th leaf}}{\text{leaf area}}$ Literature Citation: Kahan, R. P. and J. L. Libby. 1958. The Effect of Environmental Factors and Plant Age on Infection of Rice Blast Fungus, *Piricularia oryzae* Phytopathology 48: 25-30.

Late Blight of Tomato

Pathogen: Phytophthora infestans
Host: Tomato, variety Bonny Best
Growth Conditions: Tomato plants grown to the 5 leaf stage in greenhouse on Swiss Farm potting soil in 7 ounce styrafoam pots. Day temperature 20°-28° C.; night temperature 15°-20° C. Soluble 20-20-20 fertilizer applied weekly.
Treatment: Test solutions or suspensions of candidate compounds sprayed on both leaf surfaces to run-off with a No. 152 DeVilbiss atomizer at 10 psi. Formulations are prepared by dissolving compounds in methanol-Tween 20 mixture and bringing to volume with deionized water.
Inoculation: Two days after treatment a swarmspore suspension (10,000/ml) is sprayed on the lower leaf surface with a No. 152 DeVilbiss atomizer at 10 psi. The inoculum is sprayed to a point just before run-off (non-coalescing droplets). The inoculated plants are maintained at 100 percent relative humidity and 17° C. for 24 hours.
Incubation: The treated and inoculated plants are incubated in the greenhouse (15°-20° C. night temperatures; 20°-28° C. day temperatures) until symptoms appear.
Standard of Comparison: Maneb
Disease Index: percent of 3rd, 4th and 5th leaf necrotic
Literature Citation: McCallen, S. E. A. and R. H. Wellman 1943. A Greenhouse Method of Evaluating Fungicides by Means of Tomato Foliage Diseases. Contrib. Boyce Thompson Instit. 13: 93-134.

Early Blight of Tomato

Pathogen: *Alternaria solani*
Host: Tomato, variety Bonny Best
Growth Conditions: Tomato plants grown to the five leaf stage in greenhouse on Swiss Farm potting soil in 7 ounce styrafoam pots. Day temperature 20°-28° C.; night temperatures 15°-20° C. Soluble 20-20-20 fertilizer applied weekly.
Treatment: Test solutions or suspensions of candidate compounds sprayed on both leaf surfaces to run-off with a No. 152 DeVilbiss atomizer at 10 psi. Formulations are prepared by dissolving compounds in methanol-Tween 20 mixture and bringing to volume with deionized water.

Inoculation: Two days after treatment a spore suspension (10,000/ml) is sprayed on the lower leaf surface with a No. 152 DeVilbiss atomizer at 10 psi. The inoculum is sprayed to a point just before run-off (non-coalescing droplets). The inoculated plants are maintained at 100 percent relative humidity and 21° C. for 24 hours.

Incubation: The treated and inoculated plants are incubated in the greenhouse (15°-20° C. night temperatures; 20°-28° C. day temperatures) until symptoms appear.

Standard of Comparison: Maneb $$\text{Disease Index:} \frac{\text{number lesions/terminal leaflet of 3rd, 4th, 5th leaf}}{\text{leaf area}}$$

Literature Citation: McCallen, S. E. A. and R. H. Wellman, 1943. A Greenhouse Method of Evaluating Fungicides by Means of Tomato Foliage Diseases. Contrib. Boyce Thompson Instit. 13: 93–134

Powdery Mildew of Bean

Pathogen: *Erysiphe polygoni*
Host: Bean, variety Bountiful
Growth Conditions: Bean plants grown in greenhouse to point where the primary leaves are two-thirds expanded. The plants are grown on Swiss Farm potting soil in 7 ounce styrafoam pots. Dry temperatures 20°-28° C.; 15°-20° C. night temperatures. Soluble 20-20-20 fertilizer applied at weekly intervals.

Treatment: Test solutions or suspensions of candidate compounds sprayed on both leaf surfaces to run-off with a No. 152 DeVilbiss atomizer at 10 psi. Formulations are prepared by dissolving compounds in methanol-Tween 20 mixture and bringing to volume with deionized water.

Inoculation: Two days after treatment a spore suspension (5,000/ml) is sprayed on the upper leaf surface with a No. 152 DeVilbiss atomizer at 10 psi. The inoculum is sprayed to a point just before run-off (non-coalescing droplets).

Incubation: The treated and inoculated plants were incubated in the growth room (12° C. night; 18° C. day temperatures).

Standard of Comparison: Benomyl-[1-[(Butylamino)-carbonyl]-1H-benzimidazol-2-yl]carbamic acid methyl ester $$\text{Disease Index:} \frac{\text{number of lesions per primary leaf}}{\text{leaf area}}$$

Literature Citation: El-Zayat, R. J. Lukens, A. E. Dimond and J. G. Horsfall. 198. Systemic Action of Nitrophenols Against Powdery Mildew. Phytopathology 58: 434–437.

Methods and Materials

1. Protectant bioassays: As described above.
2. Systemic bioassay: Same procedure as in protectant bioassay except as indicated below.
    a. Wheat leaf rust—leaf emerging was inoculated 5 days after treatment.
    b. Rice blast—leaf emerging was inoculated 9 days after treatment.
    c. Late blight—lower leaf surface inoculated 2 days after treating upper leaf surface.
    d. Early blight—lower leaf surface inoculated 2 days after treating upper leaf surface.
    e. Powdery mildew—lower leaf surface inoculated after treating upper leaf surface.

Results

The results of all tests are given in Table 1 below. The untreated controls, test samples and positive controls are presented.

TABLE 1

| Treatment | PPM | Wheat Leaf Rust Pustules/Leaf | | Rice Blast Lesions/5th Leaf | | Late Blight (Tomato) Phytophthora % Leaf Necrosis | | Early Blight (Tomato) Alternaria Lesions/Leaf | | Bean Powdery Mildew Mildew Centers/16cm$^2$ | |
|---|---|---|---|---|---|---|---|---|---|---|---|
| | | Protectant | Systemic | Protectant | Systemic | Protectant | Systemic | Protectant | Systemic | Protectant | Systemic |
| Untreated | — | 27 | 42 | 52 | 69 | 84 | 88 | 63 | 70 | 24 | 25 |
| A43F | 1000 | 0 | 5* | <1 | 1 | 8 | 32 | 14 | 58 | <1 | 12 |
| | 500 | <1 | 15* | 0 | 9 | 8 | 60 | 29 | 45 | <1 | 14 |
| | 100 | 6 | 31* | <1 | 26 | 33 | 88 | 38 | 46 | 7 | 17 |
| | | Maneb | Carboxin** | Hinosan | Hinosan | Maneb | — | Maneb | — | Benomyl | Benomyl |
| | 1000 | — | 4 | — | 31 | — | — | 4 | — | — | 0 |
| | 100 | 0 | — | <1 | — | 11 | — | 25 | — | 0 | 7 |
| | 10 | 12 | — | 8 | — | 63 | — | 58 | — | 10 | — |
| | 1 | 20 | — | 16 | — | 77 | — | — | — | 26 | — |

*Phytotoxicity
**5,6-Dihydro-2-methyl-N-phenyl-1,4-oxathiin-3-carboxamide

From the foregoing table it appears that antibiotic A43F is:

(a) highly active against wheat leaf rust, rice blast and powdery mildew as protectants; equal to or approaching its standards of comparison as a protectant;

(b) moderately active against tomato early and late blight as a protectant;

(c) shows good activity against wheat leaf rust, rice blast and powdery mildew as a systemic and moderate activity against tomato late blight;

and that it shows very low or not evident phytotoxicity on wheat, rice, tomato and bean.

Similar tests for protectant activity of antibiotic A43F at lower concentrations, against powdery mildew of bean and rice blast are shown in Table 2 below:

| | Rice Blast | | |
|---|---|---|---|
| Compound No. | Concentration (PPM)* | Lesions per 5th Leaf | Remarks |
| A43F | 10 | 2 | no injury |
| | 1 | 4 | no injury |
| | 0.1 | 8 | no injury |

| | -continued | | |
|---|---|---|---|
| | Rice Blast | | |
| Compound No. | Concentration (PPM)* | Lesions per 5th Leaf | Remarks |
| | 0.01 | 7 | no injury |
| Untreated control | — | 22 | no injury |
| Benomyl | 100 | 0.1 | no injury |
| | 10 | 4 | no injury |
| | 1 | 4 | no injury |

*compounds dissolved in methanol and diluted with water containing Tween 20.

It should be understood that antibiotic A43F may be utilized in diverse anti-fungal formulations; solid, including finely divided powders and granular materials, as well as liquid, such as solutions, emulsions, suspensions, concentrates, emulsifiable concentrates, slurries and the like depending upon the application intended and the formulation media desired. Thus, it will be appreciated that antibiotic A43F may be employed to form anti-fungal compositions containing antibiotic A43F as the essential active ingredient thereof which compositions may also include finely divided dry or liquid diluents, extenders, fillers, conditioners and excipients, including various clays, diatomaceous earth, talc or the like or water and various organic liquids such as lower alkanols, for example, methanol, ethanol and isopropanol, and or kerosene, benzene, toluene and other petroleum distillate fractions or mixtures thereof.

The subject matter which applicants regard as their invention is particularly pointed out and distinctly claimed as follows:

1. The method of producing antibiotic A43F having the following structural formula:

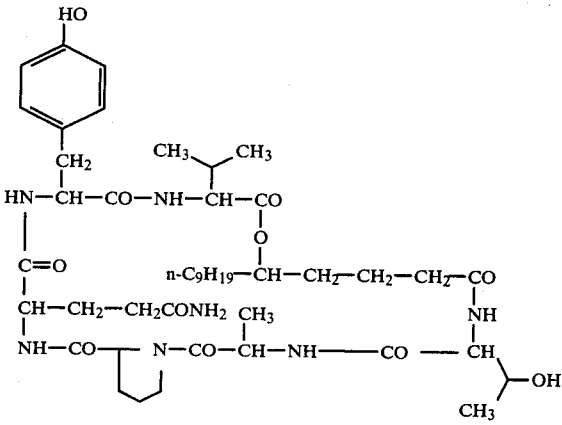

which comprises cultivating fungus species ATCC 20529 in a culture medium containing assimilable sources of carbohydrate, nitrogen and inorganic salts until a substantial amount of antibiotic activity is produced by said fungus in said culture medium and separating said antibiotic A43F from said culture medium.

2. The method of claim 1 wherein separation of antibiotic A43F from the culture medium is achieved by:
   (a) adding an equal volume of methanol to the whole broth and filtering the resulting mixture;
   (b) concentrating the filtrate from Step (a) to one-tenth the volume of the whole broth and extracting the filtrate with an equal volume of ethyl acetate;
   (c) concentrating the ethyl acetate extract from Step (b); chromatographing over silica gel eluting with methanol in ethyl acetate and separating the active fraction;
   (d) chromatographing the active fraction from Step (c) over Sephadex LH20 in a mixture of methylene chloride, hexane and methanol (10:10:1) and
   (e) evaporating the active fraction to dryness.

* * * * *